(12) United States Patent
Basta et al.

(10) Patent No.: US 7,470,254 B2
(45) Date of Patent: Dec. 30, 2008

(54) NEEDLE WITH SEALING VALVE

(75) Inventors: Michael Basta, Kulpsville, PA (US); Kevin Sanford, Chalfont, PA (US); Earl W. Voorhees, Jr., Warrington, PA (US)

(73) Assignee: Medical Components, Inc., Harleysville, PA (US)

( * ) Notice: Subject to any disclaimer, the term of this patent is extended or adjusted under 35 U.S.C. 154(b) by 68 days.

(21) Appl. No.: 10/910,684

(22) Filed: Aug. 3, 2004

(65) Prior Publication Data

US 2005/0043684 A1    Feb. 24, 2005

Related U.S. Application Data

(60) Provisional application No. 60/495,988, filed on Aug. 18, 2003.

(51) Int. Cl.
*A61M 5/178* (2006.01)

(52) U.S. Cl. .................................. 604/167.04

(58) Field of Classification Search ...............................
604/167.01–167.06, 96.01–99.02, 256, 264,
604/164.13, 160–162, 523, 158, 537; 251/149.2,
251/149.1, 298, 301
See application file for complete search history.

(56) References Cited

U.S. PATENT DOCUMENTS

| 4,387,879 | A | 6/1983 | Tauschinski | 251/149.1 |
| 4,512,766 | A | 4/1985 | Vailancourt | |
| 4,813,938 | A | 3/1989 | Raulerson | |
| 4,842,591 | A | 6/1989 | Luther | 604/283 |
| 5,062,836 | A | * | 11/1991 | Wendell | 604/167.04 |

(Continued)

FOREIGN PATENT DOCUMENTS

WO    WO 00/53254    9/2000

(Continued)

OTHER PUBLICATIONS

International Search Report, PCT/US04/26502 dated May 12, 2006, (3 pages).

(Continued)

*Primary Examiner*—Matthew F Desanto
(74) *Attorney, Agent, or Firm*—Anton P. Ness; Fox Rothschild LLP

(57) ABSTRACT

A needle assembly (100) having a hollow needle (110) with a pointed distal end (112) and a proximal end (114). The assembly also includes a needle hub (120) having a distal hub end (122) fixedly connected to the needle (110), a proximal hub end (124) having an opening, and a passageway (126) extending therethrough between the distal end and the proximal end. A valve (140) is disposed within the passageway (126), wherein the valve comprises a sealing member (142) having at least one through-opening (150) disposed therein and a plunger (146) disposed proximate the sealing member (142) and slidable between a first position wherein the at least one through-opening (150) is closed such that the hollow needle (110) and the proximal hub end (124) are not in fluid communication with each other and a second position wherein the plunger (146) biases the at least one through-opening (150) to an open position, such that the hollow needle and the proximal hub end are in fluid communication with each other. A method of using the needle assembly (100) is also disclosed.

17 Claims, 7 Drawing Sheets

U.S. PATENT DOCUMENTS

| | | | | |
|---|---|---|---|---|
| 5,085,645 | A | 2/1992 | Purdy et al. | |
| 5,092,840 | A | 3/1992 | Healy | 604/83 |
| 5,104,381 | A | 4/1992 | Gresl et al. | |
| 5,269,771 | A | 12/1993 | Thomas et al. | 604/213 |
| 5,336,192 | A | 8/1994 | Palestrant | 604/167 |
| 5,425,465 | A | 6/1995 | Healy | 215/355 |
| 5,441,487 | A | 8/1995 | Vedder | 604/167 |
| 5,456,675 | A | 10/1995 | Wolbring et al. | 604/280 |
| 5,458,640 | A * | 10/1995 | Gerrone | 604/264 |
| 5,476,475 | A | 12/1995 | Gadberry | 606/185 |
| 5,584,808 | A | 12/1996 | Healy | 604/86 |
| 5,613,663 | A * | 3/1997 | Schmidt et al. | 251/149.2 |
| 5,624,413 | A | 4/1997 | Markel et al. | |
| 5,788,215 | A | 8/1998 | Ryan | |
| 5,817,069 | A | 10/1998 | Arnett | |
| 5,893,842 | A | 4/1999 | Imbert | |
| 5,911,710 | A | 6/1999 | Barry et al. | 604/249 |
| 5,967,490 | A | 10/1999 | Pike | |
| 6,024,729 | A * | 2/2000 | Dehdashtian et al. | 604/256 |
| 6,277,100 | B1 * | 8/2001 | Raulerson et al. | 604/212 |
| 6,352,521 | B1 | 3/2002 | Prosl | 604/167.03 |
| 6,488,674 | B2 * | 12/2002 | Becker et al. | 604/533 |
| 6,585,229 | B2 | 7/2003 | Cote, Sr. et al. | 251/149.1 |
| 6,743,214 | B2 | 6/2004 | Heil et al. | 604/414 |
| 6,849,068 | B1 * | 2/2005 | Bagaoisan et al. | 604/523 |
| 7,008,404 | B2 * | 3/2006 | Nakajima | 604/158 |
| 2002/0128604 | A1 | 9/2002 | Nakajima | 604/164.01 |
| 2004/0143219 | A1 | 7/2004 | Lee et al. | 604/167 |
| 2004/0249345 | A1 | 12/2004 | Denolly | 604/167.03 |

FOREIGN PATENT DOCUMENTS

WO     WO 03/002182 A1     1/2003

OTHER PUBLICATIONS

Written Opinion, PCT/US04/26502 dated May 12, 2006 (3 pages).
Supplemental European Search Report, EP 0478 1223, dated Jul. 5, 2007 (3 pages).

* cited by examiner

NEEDLE WITH SEALING VALVE

CROSS-REFERENCE TO RELATED APPLICATION

The present application claims priority from U.S. Provisional Patent Application Ser. No. 60/495,988, filed on 18 Aug. 2003.

FIELD OF THE INVENTION

The present invention relates to a catheter insertion needle having a valve incorporated into the needle hub.

BACKGROUND OF THE INVENTION

Catheters for the introduction or removal of fluids may be located in various venous locations and cavities throughout the body for introducing or removing fluids. Such catheterization may be performed by using a single catheter having multiple lumens. A typical example of a multiple lumen catheter is a dual lumen catheter in which one lumen introduces fluids and one lumen removes fluids. Catheterization may also be performed by using separate, single lumen catheters inserted through two different incisions into an area to be catheterized. Such multiple catheter assemblies are known as TESIO® catheters sold by Medical Components, Inc. of Harleysville, Pa.

Generally, to insert any catheter in a blood vessel, the vessel is identified by aspiration using an introducer device, such as a syringe having a long hollow needle in accordance with the Seldinger technique. Typically, a needle is attached to a syringe and inserted under the patient's skin, with the plunger being withdrawn as the needle is inserted. When blood enters the syringe attached to the needle, indicating that the vessel has been found, the syringe body is removed and a thin guide wire is introduced through the needle lumen and into the interior of the vessel. The needle is then removed, leaving a portion of the guide wire within the vessel and the remainder projecting outwardly to a point beyond the surface of the patient's skin. Other guide wire introducing devices and syringes are also available. At this point, the catheter is inserted by the physician over the guide wire using one of several known techniques.

In the case of single-lumen catheters typically used in multiple catheter assemblies (e.g., a Tesio® catheter), a physician may use an introducer sheath. If a Tesio® catheter is used for hemodialysis, for example, each catheter may be inserted in two separate veins. Alternatively, each catheter may be inserted in two different locations of the same vein, such as the internal jugular vein or in a single insertion site as described in U.S. Pat. No. 5,624,413. The introducer sheath is simply a large, stiff, thin-walled tube which serves as a temporary conduit for the permanent catheter which is being placed. The introducer sheath is positioned by placing a dilator device inside of the introducer and passing both the dilator and the introducer together into the vessel over the guide wire. The guide wire, which is partially within the vessel after insertion as described above, and the dilator are then removed, leaving the thin-walled introducer sheath in place. The catheter is then placed through the introducer sheath.

In each case, the first step is aspirating the vessel or area to be catheterized prior to introducing the guide wire. This is often troublesome, especially when aspirating blood vessels, due to the flashback of blood. Arterial blood may spurt from the needle insertion point with considerable force and may contact a physician or other attendant assisting the physician, causing the risk of contamination with blood borne pathogens, such as HIV virus or hepatitis. A second problem, which is of greater concern to the patient, is exposing certain venous blood vessels or other body cavities to atmospheric pressure. Veins are often under negative pressure as blood is being drawn back to the thoracic cavity due to the process of inspiration during the breathing cycle, and a hole in a venous blood vessel could lead to air being drawn into the blood vessel, creating an air embolism.

In other types of catheterization procedures, such as a pleural effusion where fluid which collects around the lungs is drained, it is important to have a closed system guide wire introduction device which prevents atmospheric air from entering the thoracic cavity. Breathing movement creates negative pressure in the thoracic cavity, which, in combination with the air in the lungs, keeps the lungs expanded. The introduction of air into the thoracic cavity could cause the lungs to partially collapse. It is therefore important during the insertion of a guide wire for catheterization that the risk of introducing air into the thoracic cavity or a vessel be minimized.

One attempt to solve these problems is disclosed in U.S. Pat. No. 5,613,663, which discloses a valve device within a two-piece housing that requires the valve to be assembled within the device prior to assembly of the two pieces that comprise the housing. However, the valve disclosed in this patent requires arterial blood pressure to close the valve. It would be beneficial to provide a valve that is housed in a one-piece housing to facilitate manufacturing of the device, and that includes a valve closure mechanism that does not require arterial blood pressure to close the valve.

BRIEF SUMMARY OF THE INVENTION

Briefly, the present invention provides a needle assembly comprising a hollow needle having a pointed distal end and a proximal end. The assembly also includes a needle hub having a distal hub end fixedly connected to the needle, a proximal hub end having an opening, and a passageway extending therethrough between the distal end and the proximal end. A valve is disposed within the passageway, wherein the valve comprises a sealing member having at least one through-opening disposed therein and a plunger disposed proximate the sealing member and slidable between a first position wherein the at least one through-opening is closed such that the hollow needle and the proximal hub end are not in fluid communication with each other and a second position wherein the plunger biases the at least one through-opening to an open position, such that the hollow needle and the proximal hub end are in fluid communication with each other.

The present invention also provides a method of inserting a guide wire into a blood vessel. The method comprises: providing the needle assembly comprising a hollow needle having a pointed distal end and a proximal end. The assembly also includes a needle hub having a distal hub end fixedly connected to the needle, a proximal hub end having an opening a passageway extending therethrough between the distal end and the proximal end; a valve disposed within the passageway, wherein the valve comprises a sealing member having at least one through-opening disposed therein; and a plunger disposed proximate the sealing member and slidable between a first position wherein the at least one through-opening is closed such that the hollow needle and the proximal hub end are not in fluid communication with each other and a second position wherein the plunger biases the at least one through-opening to an open position, such that the hollow needle and the proximal hub end are in fluid communication with each other. The method further includes the steps of: providing a body having a luer connector extending therefrom; providing a guide wire having a distal end; releasably connecting the body to the proximal end of the hub, wherein the luer connector disposes the plunger in a distal direction, wherein the plunger biases the at least one through-opening from a closed position to an open position; inserting the pointed distal end of the needle into the blood vessel; confirming proper placement of the needle in the blood vessel by drawing blood into the body; removing the body from the needle assembly, wherein the luer connector is disposed away from the plunger, wherein the sealing member biases the plunger in a proximal direction, and wherein the at least one through-opening returns to the closed position; inserting the distal end of the guide wire into the passageway, through the at least one through-opening, through the hollow needle and into the blood vessel; and removing the needle assembly from the blood vessel by sliding the needle assembly proximally along the guide wire.

The present invention also provides a needle assembly comprising a hollow needle having a pointed distal end, a proximal end, and a longitudinal axis extending between the distal end and the proximal end. A needle hub having a distal hub end is fixedly connected to the needle. The needle hub includes a proximal hub end having an opening and a passageway extending therethrough along the longitudinal axis between the distal hub end and the proximal hub end. A valve is disposed within the passageway. The valve comprises a sealing member having at least one through-opening disposed along the longitudinal axis and a plunger disposed proximate the sealing member and slidable between a first position wherein the at least one through-opening is closed such that the hollow needle and the proximal hub end are not in fluid communication with each other and a second position wherein the plunger biases the at least one through-opening to an open position, such that the hollow needle and the proximal hub end are in fluid communication with each other.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
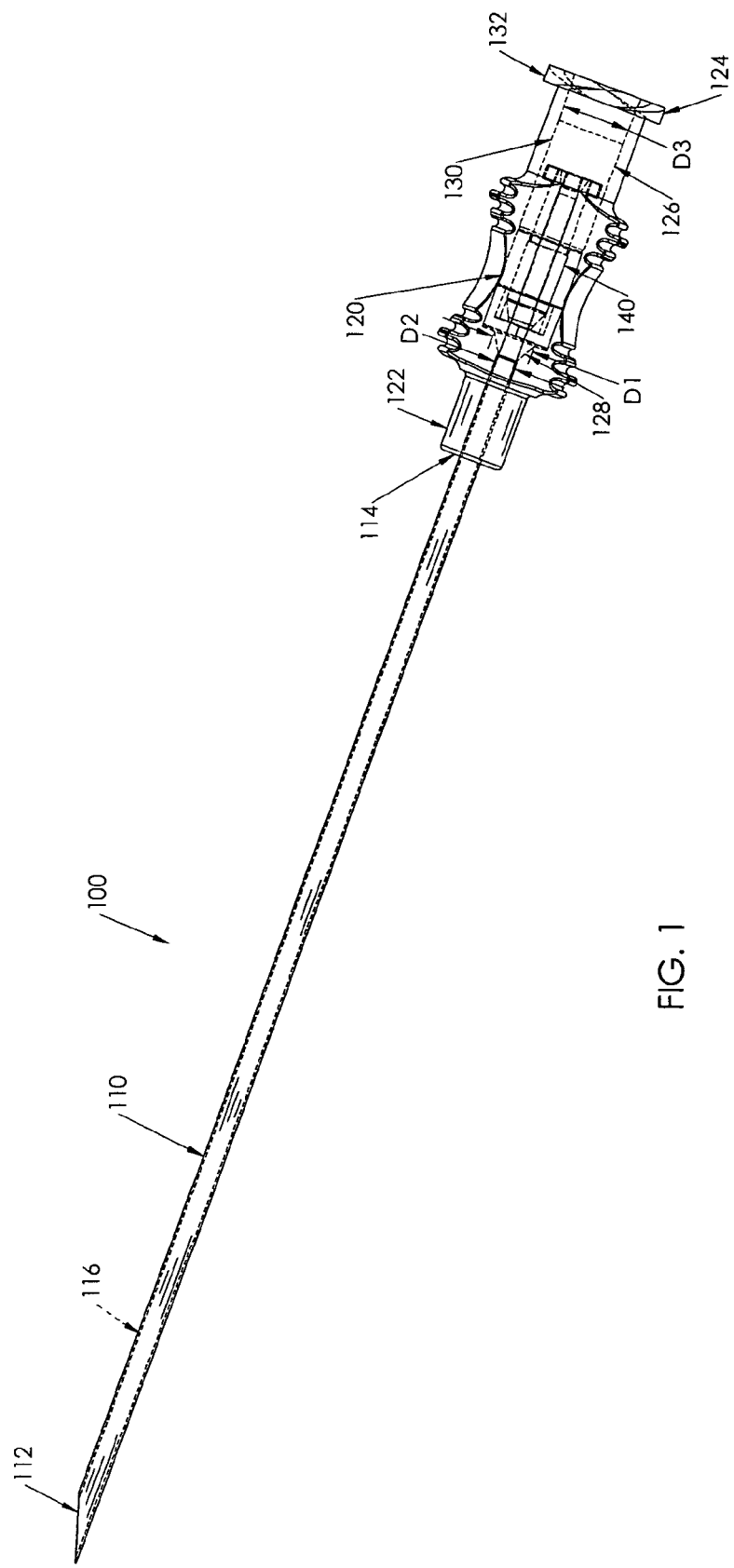
FIG. 1 is a side profile view of a needle assembly according to the present invention.

In the drawings, like numerals indicate like elements throughout. The terms "distal" and "proximal" refer to the insertion end and the connecting end, respectively, of the needle assembly according to the present invention. The terminology includes the words above specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Referring now to FIG. 1, a catheter insertion needle assembly 100 according to the present invention is shown. The needle assembly 100 includes a needle 110 having a beveled distal tip 112 and a proximal end 114. The needle 110 includes a hollow cannulating portion 116 that extends between the distal tip 112 and the proximal end 114. Preferably, the needle 110 is constructed from stainless steel or some other suitable material.

A generally hollow needle hub 120 is fixedly connected to the proximal end 114 of the needle 110. Preferably, the hub 120 is of one-piece construction for ease of manufacture and cost issues. The hub 120 includes a distal end 122 that is fixedly connected to and encompasses the proximal end 114 of the needle 110. The hub 120 also includes an open proximal end 124 and a passageway 126 extending between the proximal end 124 and the distal end 122, and in fluid communication with the cannulating portion 116 of the needle 110. A longitudinal axis 127 (FIG. 2) extends between the distal end 122 and the proximal end 124 along the passageway 126 and through the needle 110 between the distal tip 112 and the proximal end 114.

A distal end 128 of the passageway 126 is conically tapered from a larger first diameter D1 to a smaller second diameter D2 that is generally the same size as the diameter of the cannulating portion 116 of the needle 110. A proximal end 130 of the passageway 126 has a large third diameter D3 that is sized and tapered to accept a standard luer lock fitting, as is well known by those skilled in the art. The proximal end 124 also includes male threads 132 to facilitate connection of the needle assembly 100 to an external device, such as a syringe. The step between first diameter D1 and third diameter D3 defines a forward stop for the valve and the support member and can be said to comprise a first inwardly directed protrusion of third diameter D3, that portion of the passageway containing the valve 140, which includes a seal 142, a support member 144 and a plunger 146.

Figure 2:
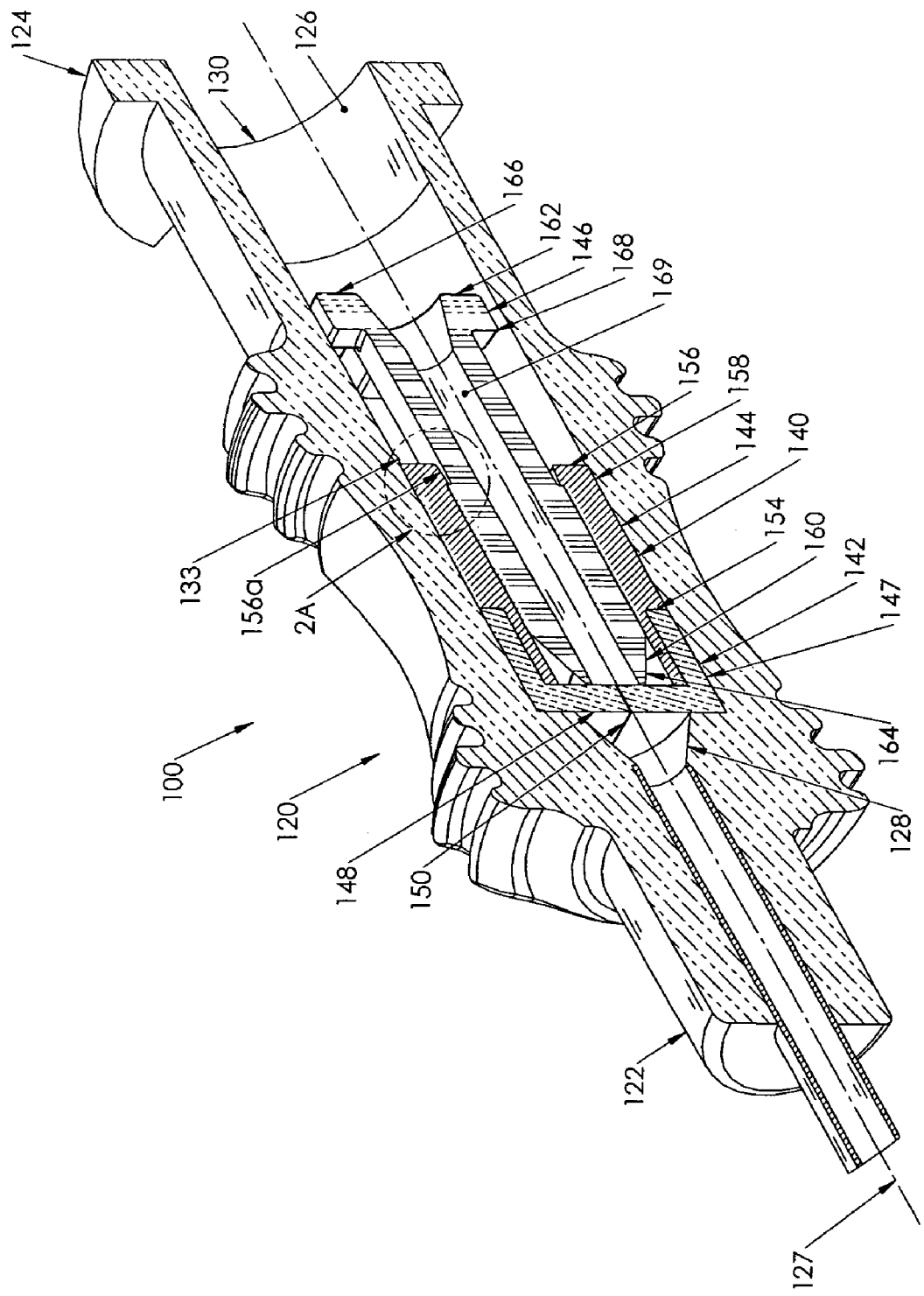
FIG. 2 is an enlarged perspective view, in section, of the needle hub shown in FIG. 1, with a hub valve in a closed position.
Figure 2A:
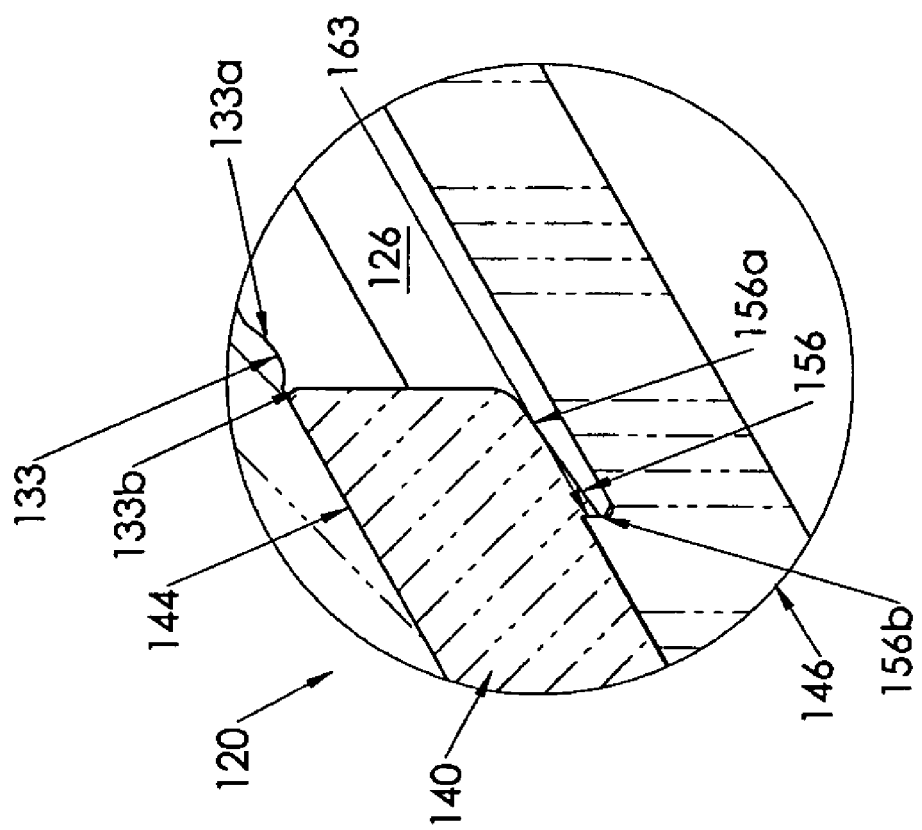
FIG. 2A is a greatly enlarged partial side profile view of FIG. 2, in section, showing retaining portions of the valve.

Referring to the enlarged sectional view of the hub 120 shown in FIG. 2, a second inwardly directed protrusion or retaining ring 133 is disposed within the passageway 126 between the distal end 128 and the proximal end 130. Referring to FIG. 2A, the retaining ring 133 includes a tapered proximal face 133a and a straight distal face 133b that extends generally perpendicular to the length of the passageway 126, and is stoppingly engaged by the proximal end surface of the support member to retain the support member and perforce the valve within the passageway distally of the retaining ring, with the forward stop comprised by the first diameter D1. Preferably, the hub 120 is constructed from CYROLITE® Med 2Acrylic-Based Multipolymer Compound, produced by Cyro Industries, Orange, CT, although those skilled in the art will recognize that other suitable materials may be used.

Referring back to FIG. 2, a valve 140 is disposed within the passageway 126. The valve 140 includes a seal 142, a support member 144, and a plunger 146. The seal 142 is disposed proximate to the distal end 128 of the passageway 126 and is generally annularly shaped, with a generally tubular side wall 147 and a closeable distal portion 148 that seals the passageway 126 to prevent fluid flow therethrough. The distal portion 148 includes a plurality of slots or through-openings 150 that extend generally radially from the center of the distal portion 148, preferably generally evenly angularly spaced, toward the sidewall 147. The seal 142 is generally disposed about the longitudinal axis 127, with the longitudinal axis 127 extending through the intersection of the through-openings 150 in the distal portion 148 of the seal 142. Preferably, three slots or through-openings 150 are present (only one through-opening 150 is shown in FIG. 2), although those skilled in the art will recognize that more or less than three through-openings 150 may be used. Preferably, the seal 142 is constructed from silicone elastomer or some other suitable material so that, when the valve 140 is opened, as will be described in more detail later herein, the through-openings 150 allow fluid flow through the seal 142.

The support member 144 is disposed within the passageway 126 just proximal of the seal 142. The support member 144 has a generally annularly shaped cross section and includes a recessed distal portion 154 sized to allow the sidewall 147 of the seal 142 to snugly surround the recessed distal portion 154 and to bias the seal 142 to a most distal position within the passageway 126. The retaining ring 133 is so shaped and positioned to allow the support member 144 to be inserted distally into the passageway 126, but restrains the support member 144 from being removed proximally from the passageway 126. Referring now to FIG. 2A, the support member 144 further includes an inwardly protruding retaining ring 156 disposed at a proximal end 158 of the support member 144. The retaining ring 156 includes a tapered proximal face 156a and a straight distal face 156b that extends generally perpendicular to the length of the passageway 126. Preferably, the support member 144 is constructed from PELLETHANE® polyurethane, CYROLITE® acrylic-based compound, or some other suitable material.

The plunger 146 includes a distal portion 160 that is disposed within the support member 144 and a proximal portion 162 that is disposed within the passageway 126 proximal of the support member 144. The plunger 146 has a generally annularly shaped cross section. A most distal end 164 of the plunger 146 is generally conically tapered, preferably at an angle approximately equal to the conical taper of the distal end 128 of the passageway 126. A most proximal end 166 of the plunger 146 includes a flange 168 that extends approximately to the sidewall 147 of the passageway 126. A plunger passageway 169 extends between the most distal end 164 and the most proximal end 166 of the plunger 146.

The proximal portion 162 of the plunger 146 has a smaller outer diameter than the distal portion 160 of the plunger 146, with a step 163 (FIG. 2A) along its outer surface defining the interface between the proximal portion 162 and the distal portion 160. When the distal portion 160 of plunger 146 is fully inserted into the support member 144, the retaining ring 156 stoppingly engages the step 163 and retains the plunger 146 within the support member 144 so that the distal portion 160 of the plunger 146 may not move proximally beyond the retaining ring 156. Thus, distal portion 160 of the plunger 146 is slidable distally between the retaining ring 156 and the distal end 128 of the passageway 126. Preferably, the plunger 146 is constructed from ISOPLAST® polyurethane, or some other suitable material.

Figure 3:
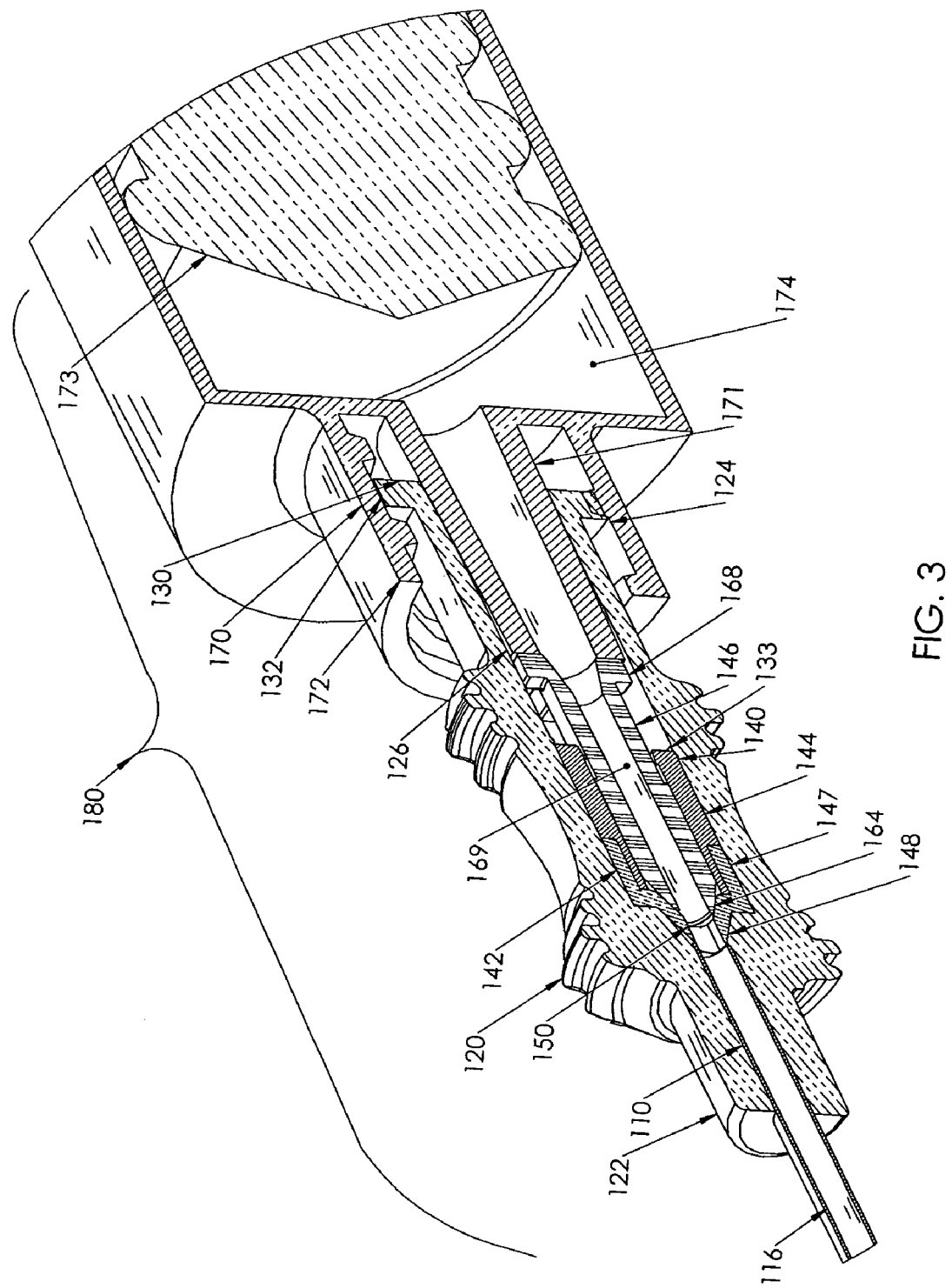
FIG. 3 is a perspective view, in section, of the needle hub of FIG. 2, with a syringe opening the hub valve.

In operation, as shown in FIG. 3, a syringe 170 is releasably connected to the proximal end 124 of the hub 120. Preferably, the syringe 170 includes a male luer connector 171 that is sized to sealably fit into the passageway 126 from the proximal end 130 of the passageway 126. Also preferably, the syringe 170 includes female threads 172 that enable the syringe 170 to threadably engage the male threads 132 at the proximal end 124 of the hub 120. The luer connector 171 engages the flange 168 and disposes the flange 168, along with the plunger 146, in a distal direction along the passageway 126. The distal most distal end 164 of the plunger 146 engages the distal portion 148 of the seal 144, opening valve 140 through the seal 142 along the through-openings 150. The passageway 126 at the proximal end 124 of the hub 120 is now in fluid communication with the hollow cannulating portion 116 of the needle 110.

With the syringe 170 connected to the needle assembly 100, forming a syringe assembly 180, the syringe assembly 180 is inserted into a patient according to known methods. When the inserting physician believes that the syringe assembly 180 is properly inserted into a desired blood vessel, the physician draws back on the syringe plunger 173, drawing a suction on the passageway 126 and the hollow cannulating portion 116 of the needle 110. The suction draws blood from the vessel through the cannulating portion 116 of the needle 110, through the now open valve 140 and the passageway 126 and into the syringe chamber 174. When the physician confirms proper placement of the needle assembly 100 by the blood flashback in the syringe chamber 174, the physician may then depress the plunger 173, forcing the blood back through the needle assembly 100 and into the vessel so that the syringe 170 may be removed from the needle assembly 100.

As the syringe 170 is removed from the needle assembly 100 by unthreading the female threads 172 on the syringe 170 from the male threads 132 on the hub 120 and sliding the syringe 170 proximally relative to the needle assembly 100, the luer connector 171 is disposed away from the flange 168. The resiliency of the silicon or other material comprising the seal 142 allows the distal portion 148 of the seal 142 to bias the plunger 146 proximally, allowing the distal portion 148 of the seal 142 to close, shutting off fluid communication between the passageway 126 and the cannulating portion 116 of the needle 110.

Figure 4:
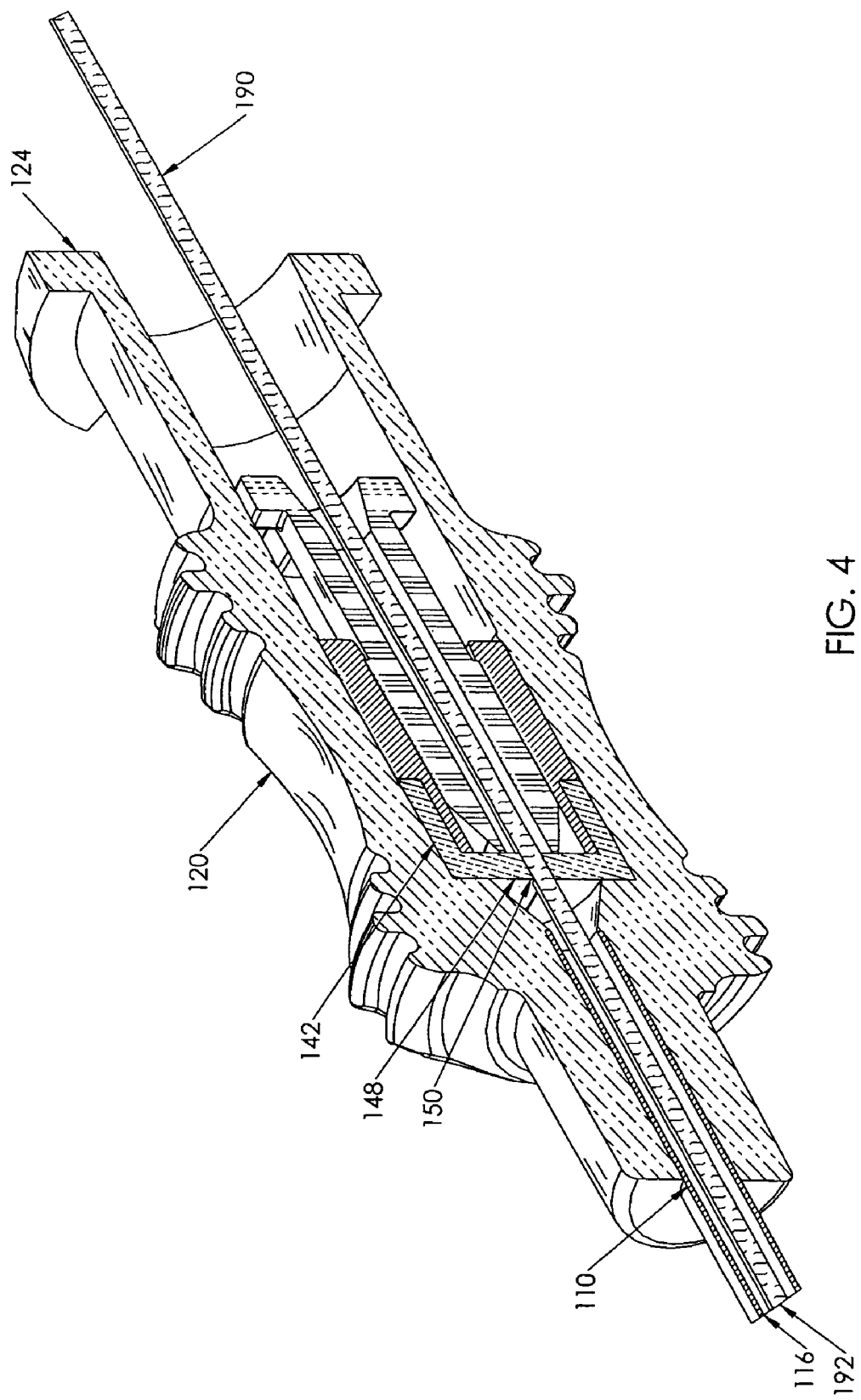
FIG. 4 is a perspective view, in section, of the needle hub of FIG. 2, with a guide wire inserted through the hub valve.

The syringe 170 is now removed, and blood flow from the blood vessel through the needle assembly 110 is prevented by the seal 142 that is now closed. As shown in FIG. 4, a guide wire 190 is inserted into the proximal end 124 of the hub 120 according to known techniques. The distal end 192 of the guide wire 190 is able to be forced through the through-openings 150 in the distal portion 148 of the seal 142 so that the guide wire 190 may be partially inserted into the blood vessel through the cannulating portion 116 of the needle 110. The resilience of the seal 142 seals the seal 142 around the guide wire 190 so that blood is restricted from flowing proximally through the seal 142.

Once the guide wire 190 is in a desired location within the blood vessel, the needle assembly 100 may be removed from the patient by sliding the needle assembly 100 proximally along the guide wire 190. With the guide wire 190 in place, a catheter or other device (not shown) may be inserted into the blood vessel along the guide wire 190.

Figure 5:
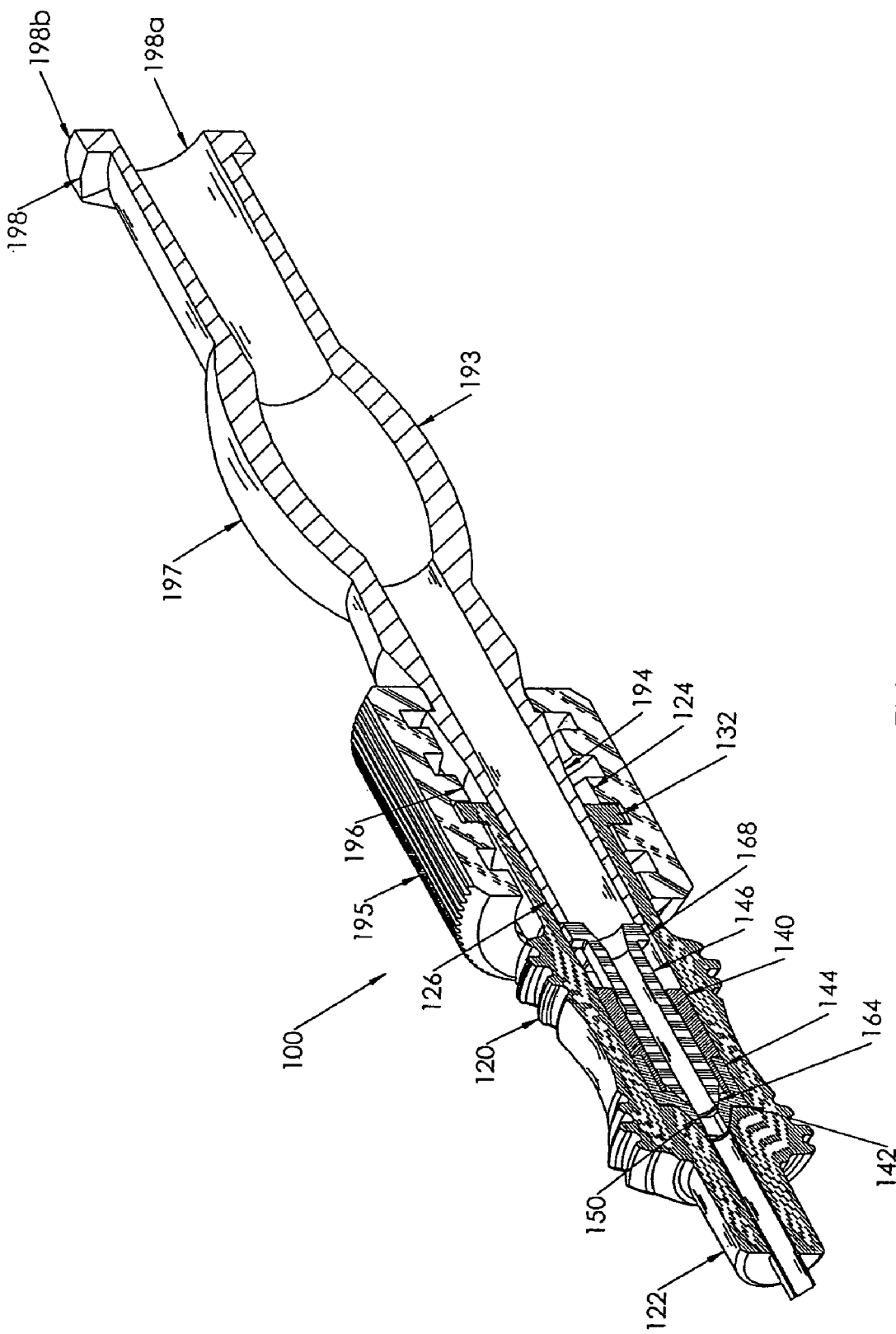
FIG. 5 is a perspective view, in section, of the needle hub of FIG. 2, with a bulb opening the hub valve.

Those skilled in the art will recognize that a device other than the syringe 170 may be connected to the needle assembly 100. For example, as shown in FIG. 5, a bulb 193 may be used. The bulb 193 is preferably of unitary construction and is constructed from a transparent or at least a translucent material, such as nylon or LEXAN® polycarbonate. The bulb 193 includes a male luer fitting 194 that is configured to fit into the passageway 126 in the same manner as the luer fitting 171 on the syringe 170, as described above, and to open the valve 140 as described above. The bulb 193 includes a swivel lock 195 having female threads 196 that allow the bulb 193 to be threadingly connected to the needle assembly 100 via the male threads 132 at the proximal end 124 of the hub 120. A bulb portion 197 allows any blood that flashes into the bulb 193 through the needle assembly 110 to be easily seen due to the magnification properties of the bulbous shape of the bulb portion 197. The bulb 193 also includes a proximal end 198 that includes a female luer fitting 198*a* and a male thread 198*b* for connection of an exterior device, such as the syringe 170, to the bulb 193.

In operation, the bulb 193 is releasably connected to the needle hub 120 by inserting the male luer fitting 194 into the passageway 126 and engaging the thread 196 on the swivel lock 195 with the thread 132 on the hub 120. The male luer fitting 194 engages the plunger 146, forcing the plunger 146 distally toward the distal end 122 of the hub 120. The plunger 146 engages the seal 142, opening the valve 140 through the seal 142 along the through-openings 150.

Although not shown, the syringe 170 may be connected to the proximal end 198 of the bulb 193 by inserting the male luer fitting 171 into the female luer fitting 198*a* and engaging the female thread 172 with the male thread 198*b*. The cannulating portion 116 of the needle 110 is now in fluid communication with the syringe chamber 174.

The needle assembly 100 is next inserted into the patient according to known techniques. The syringe chamber 174 is drawn proximally, drawing blood from the patient, through the cannulating portion 116 of the needle 110, through the valve 140, and into the bulb 173, where the inserting physician can see the blood flash into the bulb portion 197 to confirm that the needle 110 is inserted properly.

The bulb 193 is then disconnected from the needle assembly 100 and the valve 140 closes as described above. The guide wire 170 may now be inserted, as is also described above.

Figure 6:
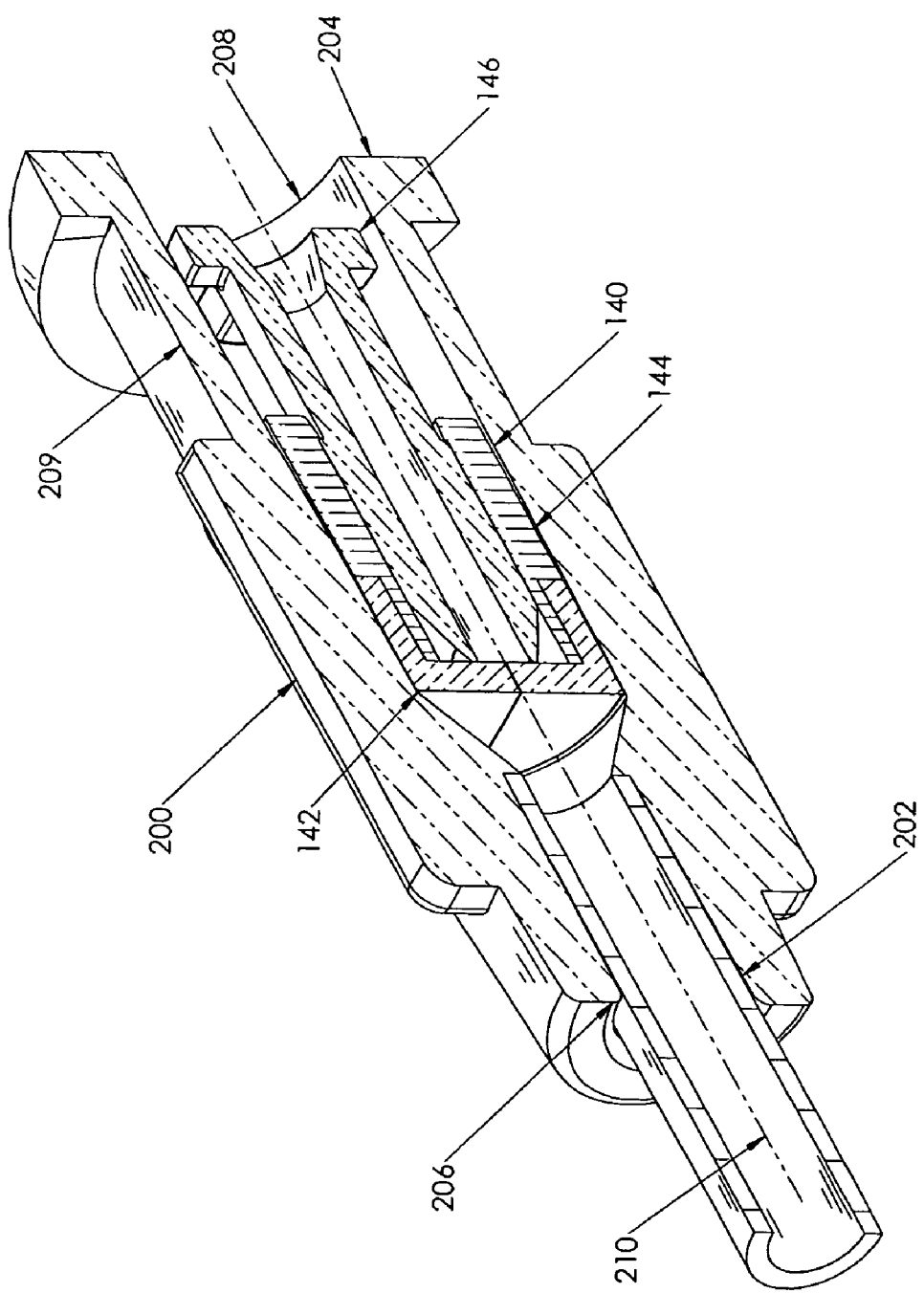
FIG. 6 is a perspective view, in section, of an alternate embodiment of the present invention.

Those skilled in the art will recognize that the valve 140 may be used in other devices than the needle assembly 100 as described above. For example, the valve 140 may be inserted into a luer 200, as shown in FIG. 6. The luer 200 may be connected to a proximal end of a catheter lumen 202 and includes a proximal luer end 204, a distal luer end 206, and a longitudinal passage 208 extending between the proximal luer end 204 and the distal luer end 206. A luer wall 209 forms the luer passage 208. The luer 200 also includes a longitudinal axis 210 extending through the passage 208 between the proximal luer end 204 and the distal luer end 206.

The valve 140 is disposed within the longitudinal passage 208 such that the seal 142 is disposed distal of the plunger 146. The support member 144 is disposed between the plunger 146 and the luer wall 209. Operation of the valve 140 within the luer 200 is the same as the operation of the valve 140 within the needle hub 120 as described above.

Further, the present invention is not limited to a syringe or a luer. Those skilled in the art will recognize that the valve 140 may be incorporated into any luer lock-type pathway that requires unobstructed flow when a male luer is inserted into the pathway and positive closure when the male luer is removed from the pathway.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A needle assembly comprising:
    a hollow needle having a pointed distal end and a proximal end;
    a needle hub having a distal hub end fixedly connected to the needle, a proximal hub end having an opening, and a passageway extending therethrough between the distal hub end and the proximal hub end;
    a valve disposed within the passageway, wherein the valve comprises a sealing member having at least one through-opening disposed therein, and the sealing member including a proximal portion defining a recess thereinto from a proximal valve end;
    a non-resilient support member disposed in the passageway proximally of, adjacent to and in supportive engagement with the sealing member such that the proximal portion of the sealing member surrounds a distal end of the support member and the support member is secured in the passageway against proximal movement with respect to the passageway; and
    a plunger disposed in and secured within the passageway proximate the sealing member and the support member and slidable between a first position wherein the at least one through-opening is closed such that the hollow needle and the proximal hub end are not in fluid communication with each other and a second position wherein the plunger biases the at least one through-opening to an open position, such that the hollow needle and the proximal hub end are in fluid communication with each other.

2. The needle assembly according to claim 1, wherein the sealing member, the support member and the plunger are wholly disposed within the passageway, and the passageway includes a first inwardly directed protrusion proximate a distal end of the passageway to provide a forward stop for the valve, and a second inwardly directed protrusion proximally from the first inwardly directed protrusion and so positioned and shaped to permit insertion of the valve and the support member therepast during assembly and to thereafter be engaged by the support member to retain the support member and the valve distally thereof and between the first and second inwardly directed protrusions.

3. The needle assembly according to claim 2, wherein the support member includes an inwardly directed protrusion so positioned and shaped to permit insertion of the distal portion of the plunger therepast during assembly, and thereafter to maintain the plunger within the needle hub while permitting movement of the plunger between its first and second positions in stoppable cooperation with an outwardly directed protrusion along the distal portion of the plunger.

4. The needle assembly according to claim 1, wherein the needle hub further comprises a longitudinal axis extending therethrough.

5. The needle assembly according to claim 4, wherein the seal is generally disposed about the longitudinal axis.

6. The needle assembly according to claim 1, wherein the needle hub is made as a single unitary piece defining the entire passageway into which the valve, support member and plunger are inserted.

7. The needle assembly according to claim 1, further comprising a bulb releasably connected to the proximal end of the needle hub.

8. A method of inserting a guide wire into a blood vessel comprising:
    providing the needle assembly according to claim 1;
    providing a body having a luer connector extending therefrom;

providing a guide wire having a distal end;
releasably connecting the body to the proximal end of the hub, wherein the luer connector disposes the plunger in a distal direction, wherein the plunger biases the at least one through-opening from a closed position to an open position;
inserting the pointed distal end of the needle into the blood vessel;
confirming proper placement of the needle in the blood vessel by drawing blood into the body;
removing the body from the needle assembly, wherein the luer connector is disposed away from the plunger, wherein the sealing member biases the plunger in a proximal direction, and
wherein the at least one through-opening returns to the closed position;
inserting the distal end of the guide wire into the passageway, through the at least one through-opening, through the hollow needle and into the blood vessel; and
removing the needle assembly from the blood vessel by sliding the needle assembly proximally along the guide wire.

9. The method according to claim 8, wherein providing the body comprises providing a syringe.

10. The method according to claim 8, wherein providing the body comprises providing a bulb.

11. The method according to claim 10, further comprising connecting a syringe to the bulb.

12. A needle assembly comprising:
a hollow needle having a pointed distal end, a proximal end, and a longitudinal axis extending between the distal end and the proximal end;
a needle hub having a distal hub end fixedly connected to the needle, a proximal hub end having an opening, and a passageway extending therethrough along the longitudinal axis between the distal hub end and the proximal hub end;
a valve disposed within the passageway, wherein the valve comprises a sealing member having at least one through-opening disposed along the longitudinal axis, and the sealing member including a proximal portion defining a recess thereinto from a proximal valve end;
a non-resilient support member disposed in the passageway proximally of, adjacent to and in supportive engagement of the sealing member such that the proximal portion of the sealing member surrounds a distal end of the support member and the support member is secured in the passageway against proximal movement with respect to the passageway; and
a plunger disposed in and secured within the passageway proximate the sealing member and slidable between a first position wherein the at least one through-opening is closed such that the hollow needle and the proximal hub end are not in fluid communication with each other and a second position wherein the plunger biases the at least one through-opening to an open position, such that the hollow needle and the proximal hub end are in fluid communication with each other.

13. The needle assembly according to claim 12, wherein the sealing member, the support member and the plunger are wholly disposed within the passageway, and the passageway includes a first inwardly directed protrusion proximate a distal end of the passageway to provide a forward stop for the valve, and a second inwardly directed protrusion proximally from the first inwardly directed protrusion and so positioned and shaped to permit insertion of the valve and the support member therepast during assembly and to thereafter be engaged by the support member to retain the support member and the valve distally thereof and between the first and second inwardly directed protrusions.

14. The needle assembly according to claim 13, wherein the support member includes an inwardly directed protrusion so positioned and shaped to permit insertion of the distal portion of the plunger therepast during assembly, and thereafter to maintain the plunger within the needle hub while permitting movement of the plunger between its first and second positions in stoppable cooperation with an outwardly directed protrusion along the distal portion of the plunger.

15. The needle assembly according to claim 12, wherein the needle hub is made as a single unitary piece defining the entire passageway into which the valve, support member and plunger are inserted.

16. The needle assembly according to claim 12, further comprising a bulb releasably connected to the proximal end of the needle hub.

17. A combination passageway and valve comprising:
a passageway comprising:
a first end;
a second end;
a longitudinal axis extending between the first end and the second end;
a passage fluidly communicating the first end and the second end; and
a wall forming the passageway; and
a valve disposed in the passage between the first end and the second end, wherein the valve comprises:
a sealing member having at least one through-opening disposed along the longitudinal axis;
a support member disposed in the passageway proximally of, adjacent to and supportive of the valve such that a proximal end of the valve surrounds a distal end of the support member and the support member is secured in the passageway against proximal movement with respect to the passageway; and
a plunger disposed proximate the sealing member and the support member and slidable between a first position wherein the at least one through-opening is closed such that the first end and the second end are not in fluid communication with each other and a second position wherein the plunger biases the at least one through-opening to an open position, such that the first end and the second end are in fluid communication with each other,
wherein the sealing member, the support member and the plunger are wholly disposed within the passageway, and the passageway includes a first inwardly directed protrusion proximate the distal end of the passageway to provide a forward stop for the valve, and a second inwardly directed protrusion proximally from the first inwardly directed protrusion and so positioned and shaped to permit insertion of the valve and the support member therepast during assembly and to thereafter be engaged by the support member to retain the support member and the valve distally thereof and between the first and second inwardly directed protrusions.

* * * * *